United States Patent
Nettleton et al.

(10) Patent No.: US 9,974,879 B2
(45) Date of Patent: May 22, 2018

(54) CATALYTIC FRAGRANCE BURNER ASSEMBLY AND A METHOD OF MANUFACTURE THEREOF

(71) Applicant: Ashleigh & Burwood Ltd., West Molesey, Surrey (GB)

(72) Inventors: John Nettleton, Walton-on-Thames (GB); Sivakumar Kandiah, West Molesey (GB)

(73) Assignee: ASHLEIGH & BURWOOD LTD, Surrey (GB)

( * ) Notice: Subject to any disclaimer, the term of this patent is extended or adjusted under 35 U.S.C. 154(b) by 628 days.

(21) Appl. No.: 14/558,477

(22) Filed: Dec. 2, 2014

(65) Prior Publication Data
US 2015/0151018 A1    Jun. 4, 2015

(30) Foreign Application Priority Data

Dec. 3, 2013  (GB) .................................. 1321309.5
Apr. 4, 2014  (GB) .................................. 1406113.9

(51) Int. Cl.
| | |
|---|---|
| *A61L 9/03* | (2006.01) |
| *F23D 3/02* | (2006.01) |
| *B01J 23/10* | (2006.01) |
| *B01J 23/34* | (2006.01) |
| *B01J 23/42* | (2006.01) |
| *B01J 23/44* | (2006.01) |
| *B01J 23/835* | (2006.01) |
| *B01J 35/02* | (2006.01) |
| *F23D 3/40* | (2006.01) |

(52) U.S. Cl.
CPC ............... *A61L 9/037* (2013.01); *B01J 23/10* (2013.01); *B01J 23/34* (2013.01); *B01J 23/42* (2013.01); *B01J 23/44* (2013.01); *B01J 23/835* (2013.01); *B01J 35/02* (2013.01); *F23D 3/02* (2013.01); *F23D 3/40* (2013.01); *F23D 2900/03081* (2013.01); *Y10T 29/49348* (2015.01); *Y10T 428/249953* (2015.04)

(58) Field of Classification Search
USPC ........................................... 431/323; 422/126
See application file for complete search history.

(56) References Cited

U.S. PATENT DOCUMENTS

| | | | |
|---|---|---|---|
| 4,058,485 | A | 11/1977 | Cheung |
| 5,679,441 | A | 10/1997 | Saelens et al. |

(Continued)

FOREIGN PATENT DOCUMENTS

| | | |
|---|---|---|
| EP | 0277875 A1 | 10/1990 |
| EP | 0405481 | 1/1991 |

(Continued)

OTHER PUBLICATIONS

United Kingdom Search Report in Application No. GB1421393.8, dated May 20, 2015, 3 pgs.

(Continued)

*Primary Examiner* — Avinash Savani
(74) *Attorney, Agent, or Firm* — Maschoff Brennan

(57) ABSTRACT

A catalytic fragrance burner assembly, comprising: a porous core of sintered material; a catalyst, deposited on or around the core; and a wick, in communication with the porous core, and arranged to draw fuel to the core.

20 Claims, 5 Drawing Sheets

(56) References Cited

U.S. PATENT DOCUMENTS

| | | | |
|---|---|---|---|
| 6,162,046 A * | 12/2000 | Young | F23D 3/02 126/45 |
| 6,537,061 B1 | 3/2003 | Gomez et al. | |
| 7,137,811 B2 * | 11/2006 | Lehoux | A01M 1/2088 431/268 |
| 7,686,668 B1 * | 3/2010 | Butler | A63H 27/10 239/1 |
| 9,279,583 B2 * | 3/2016 | Pisklak | F23D 3/40 |
| 2002/0086253 A1 * | 7/2002 | Young | F23D 3/02 431/11 |
| 2005/0074370 A1 * | 4/2005 | Yuan | A61L 9/037 422/126 |
| 2005/0147540 A1 * | 7/2005 | Huang | A61L 9/037 422/125 |
| 2006/0219962 A1 * | 10/2006 | Dancs | A01M 1/2077 250/577 |
| 2007/0134607 A1 * | 6/2007 | Chen | F23D 3/18 431/299 |
| 2007/0166587 A1 * | 7/2007 | Nagao | H01M 8/04022 429/415 |
| 2007/0202450 A1 | 8/2007 | Pisklak et al. | |
| 2008/0014539 A1 | 1/2008 | Atreya | |
| 2008/0090188 A1 * | 4/2008 | Pisklak | F23D 3/40 431/7 |
| 2012/0245024 A1 * | 9/2012 | Chaput | B01J 21/16 502/339 |
| 2017/0074508 A1 * | 3/2017 | Pisklak | F23D 3/02 |

FOREIGN PATENT DOCUMENTS

| | | |
|---|---|---|
| EP | 2772302 A1 | 3/2014 |
| FR | 2483782 A1 | 6/1980 |
| FR | 2 905 164 A1 | 2/2008 |
| FR | 2 950 257 A1 | 3/2011 |
| GB | 760796 A | 11/1956 |
| GB | 1247406 A | 9/1971 |
| JP | S5021225 A | 3/1975 |
| JP | 2005095846 A | 4/2005 |
| WO | 2006134403 A3 | 12/2006 |
| WO | 2008023111 A1 | 2/2008 |

OTHER PUBLICATIONS

European Examination Report in Application No. 14 195 917.1-1370, dated Apr. 22, 2016, 4 pages.
O. Sanz, F.J. Echave, M. Sanchez, A. Monzon, M. Montes, "Aluminium foams as structured supports for volatile organic compounds (VOCs) oxidation", Applied Catalysis A: General 340, (2008) 125-132.
A.N. Pestryakov, E.N. Yurchenko, A.E. Feofilov, "Foam-metal catalysts for purification of waste gases and neutralization of automotive emissions", Catalysis Today 29 (1996) 67-70.
A. Sirijaruphana, J. G. Goodwin Jr., R. W. Rice, D. Wei, K. R. Butcher, G. W. Roberts, J. J. Spivey, "Metal foam supported Pt catalysts for the selective oxidation of CO in hydrogen", Applied Catalysis A: General 281 (2005) 1-9.
F.J. Echave, O. Sanz, I. Velasco, J.A. Odriozola, M. Montes, "Effect of the alloy on micro-structured reactors for methanol steam reforming",Catalysis Today 213 (2013) 145-154.
S. Cimino, R. Gerbasi, L. Lisi, G. Mancino, M. Musiani, L. Vazquez-Gomez, E. Verlato, "Oxidation of CO and CH4 on Pd-Fecralloy foam catalysts prepared by spontaneous deposition", Chemical Engineering Journal, in press, 2013.
Y. L1,L. Zhu, K. Van, J. Zheng, B. H. Chen, W. Wang, "A novel modification method for nickel foam support and synthesis of a metal-supported hierarchical monolithic Ni@Pd catalyst for benzene hydrogenation", Chemical Engineering Journal 226 (2013) 166-170.
L. Sang, B. Sun, H. Tan, C. Ou, Y. Wu, C. Ma, "Catalytic reforming of methane with C02 over metal foam based monolithic catalysts", International Journal of Hydrogen Energy 37 (2012) 13037-13043.
A. Löfberg, A. Essakhia, S. Paula, Y. Swesi, M.-L. Zanota, V. Meille, I. Pitault, P. Supiota, B. Mutel, V. Le Courtois, E. Bordes-Richard, "Use of catalytic oxidation and dehydrogenation of hydrocarbons reactions to highlight improvement of heat transfer in catalytic metallic foams", Chemical Engineering Journal 176-177 (2011) 49-56.
N. Gokon, Y. Yamawaki, O. Nakazawa, T. Kodama, "Kinetics of methane reforming over Ru/y-Al2O3-catalyzed metallic foam at 650-900° C. for solar receiver-absorbers", International Journal of Hydrogen Energy 36 (2011) 203-215.
J. Papavaslliou, G. Avgouropoulos, T. Ioannides, "In situ combustion synthesis of structured Cu—Ce—O and Cu—Mn—O catalysts for the production and purification of hydrogen", Applied Catalysis B: Environmental 66 (2006) 168-174.
K. A. Williams, L. D. Schmidt, "Catalytic autoignition of higher alkane partial oxidation on Rh-coated foams", Applied catalysts A: General 299 (2006) 30-45.
I. Cerri, G. Saracco, V. Specchia, "Methane combustion over low-emission catalytic foam burners", Catalysis Today 60 (2000) 21-32.
R. Spinicci, M. Faticanti, P. Marini, S. De Rossi, P. Porta, "Catalytic activity of LaMn03 and LaCo03 perovskites towards VOCs combustion", Journal of Molecular Catalysis A: Chemical 197 (2003) 147-155.
H.-G. Lintz, K. Wittstock, "The oxidation of solvents in air on oxidic catalysts—formation of intermediates and reaction network", Applied Catalysis A: General 216 (2001) 217-225.
Jose Manuel Gallardo-Amores, Tiziana Armaroli, Gianguido Ramis, Elisabetta Finocchio, Guido Busca, "A study of anatase-supported Mn oxide as catalysts for 2-propanol oxidation", Applied Catalysis B: Environmental 22 (1999) 249-259.
Extended European Search Report dated May 4, 2015 as received in Application No. 14195917.1.
Search Report dated Jun. 16, 2014 in GB application No. 1321309.5.
Search Report dated Oct. 7, 2014 in GB application No. 1406114.7.
Search Report dated Oct. 7, 2014 in GB application No. 1406113.9.

* cited by examiner

CATALYTIC FRAGRANCE BURNER ASSEMBLY AND A METHOD OF MANUFACTURE THEREOF

CROSS-REFERENCE TO RELATED APPLICATIONS

This application is a convention priority of United Kingdom Patent Application No. 1321309.5, filed Dec. 3, 2013, titled A Catalytic Fragrance Burner Assembly and a Method of Manufacture Thereof, and is a convention priority of United Kingdom Patent Application No 1406113.9, filed Apr. 4, 2014, titled A Catalytic Fragrance Burner Assembly and a Method of Manufacture Thereof, all of which are incorporated herein by reference in their entireties.

FIELD

The present application relates to a catalytic fragrance burner assembly and a method of manufacture of a catalytic fragrance burner assembly.

BACKGROUND

Catalytic fragrance burners are used to disperse a fragrance in a room. Such burners include a ceramic stone which is impregnated with a suitable catalyst, such as platinum, palladium or lanthanum. An alcohol-based fuel is fed to the ceramic stone using a wick. The wick is arranged to hang within a fuel reservoir, in order to draw fuel to the ceramic stone. The burner is typically started by holding a naked flame to the ceramic stone. This causes the fuel to catch alight, which produces a relatively high (perhaps 4 to 6 inches) naked flame. As the ceramic stone heats up, catalytic combustion occurs in and around the stone. After around three minutes or so, the ceramic stone reaches an operating temperature of around 330° C., after which the naked flame can be extinguished. Catalytic combustion continues in and around the stone, and the device continues to operate without a flame.

A typical catalytic fragrance burner 100 is shown in cross-section in FIG. 1. The burner 100 includes an outer ceramic stone 102 and an inner ceramic stone 104. The outer stone 102 is coated with a catalyst coating 106 and the inner stone 104 is coated with catalyst coating 108, both of which are made from the same catalyst. The outer stone 106 includes a wick receiving portion 110. The fragrance burner 100 also includes a wick 112, which is a length of rope, formed in a loop so that both ends 114, 116 are located in the wick receiving portion 110. The burner 100 also includes a metal sheath 118, which fits around the outer stone 102. The metal sheath has an opening in its base having a diameter slightly narrower than the wick receiving portion, so as to lightly grip the wick 112. The burner 100 also includes a stone locking member 120, which clips into the metal sheath 118 and holds the inner stone 104 in position in the outer stone 102. The whole arrangement the sits on top of the neck of a fuel reservoir (not shown). Alternative designs include a one-piece ceramic stone, rather than two pieces of ceramic.

The above-described burner has a number of problems. Firstly, the ceramic stone has a fairly low porosity, and the pores are very small. As the fuel burns, incompletely combusted fragrance builds up, causing charring and causing the fuel to block the pores. The ceramic stone can not easily be cleaned, and as a result, the stone must be periodically replaced. Furthermore, when the device is started, it can take up to three minutes for the stone to get up to operating temperature, and an open flame is present during this time. This is both dangerous to the user, and time consuming. Furthermore, while heating up, the fuel is consumed at a much greater rate. Accordingly, there is a need for improved catalytic fragrance burners.

US Patent Application Publication No. US 2008/0090188A1 discloses one such example of an improved catalytic burner. The burner includes a non-porous substrate which is coated in a suitable catalyst. The wick is positioned in communication with the substrate. This device operates in the same way as the aforementioned prior art, but avoids the issue of pore clogging by using a non-porous catalyst substrate.

Some embodiments of the present invention provides an alternative catalytic fragrance burner assembly.

SUMMARY

Some embodiments provide a catalytic fragrance burner assembly, comprising: a porous core of sintered material; a catalyst, deposited on or around the core; and a wick, in communication with the porous core, and arranged to draw fuel to the core.

Some embodiments provide a catalytic burner assembly, comprising: a porous metal core; a catalyst, deposited on or around the core; and a wick, in communication with the porous core, and arranged to draw fuel to the core. The sintered material may be sintered metal. The sintered metal may bronze.

Some embodiments provide a catalytic burner assembly, comprising: a porous core of sintered material; a catalyst, deposited on or around the core; and a wick, in communication with the porous core, and arranged to draw fuel to the core.

The following optional features may be incorporated into any or all of the embodiments described herein.

The porous core preferably has a porosity greater than 30% and more preferably between 30% and 60%.

The porous core preferably has pore sizes from 15 to 150 microns and more preferably from 30 to 100 microns.

The catalyst may be deposited on the core.

The burner assemblies may further comprise a metal substrate, positioned on or adjacent the porous core; wherein the catalyst is deposited on the metal substrate.

The porous core may be substantially cylindrical and/or may comprise a void, located at an end of the core, at least a first end of the wick being positioned within said void.

The catalyst may be platinum, palladium, lanthanum or a manganese oxide.

The burner assemblies may further comprising: a housing, arranged to hold the core and the wick together. Each housing may be a hollow metal bolt.

Some embodiments provide a catalytic fragrance burner, comprising: the burner assembly of the first aspect of the invention; a fuel reservoir, having an opening, wherein, in use, the burner assembly is positioned in the opening, and an end of the wick is positioned within the fuel reservoir.

Some embodiments provide a method of manufacturing a catalytic fragrance burner assembly, comprising: providing a porous core of sintered material; providing a catalyst on or around the core; and providing a wick in a communication with the core.

Some embodiments provide a porous core of sintered material, suitable for use in a catalytic fragrance burner, the core having a catalyst deposited thereon.

Other features and advantages of the present invention will be apparent from the appended claims.

BRIEF DESCRIPTION OF THE DRAWINGS

The drawings will now be described, by way of example only, and with reference to the accompanying drawings, in which.

DETAILED DESCRIPTION

Figure 1:
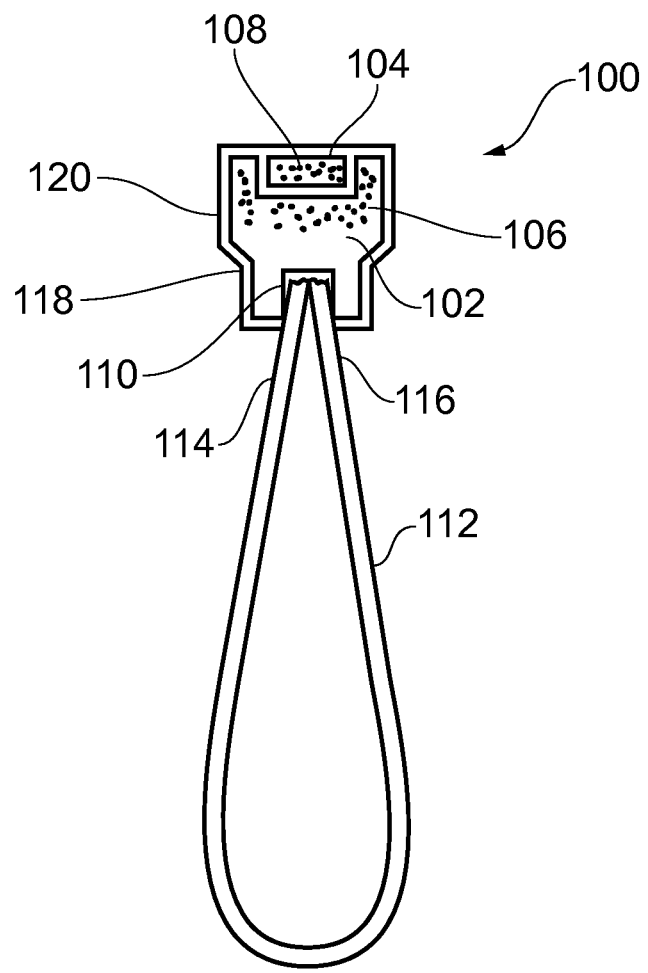
FIG. 1 shows a cross-section through a fragrance burner assembly known from the prior art.
Figure 2:
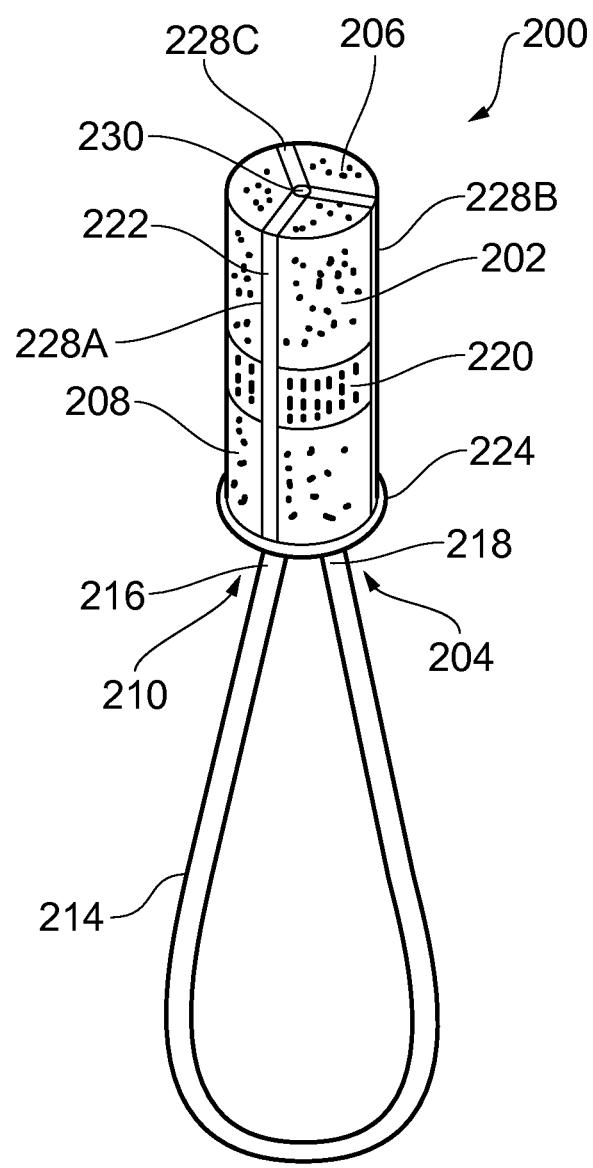
FIG. 2 shows a perspective view a fragrance burner assembly in accordance with a some embodiments described herein.
Figure 3:
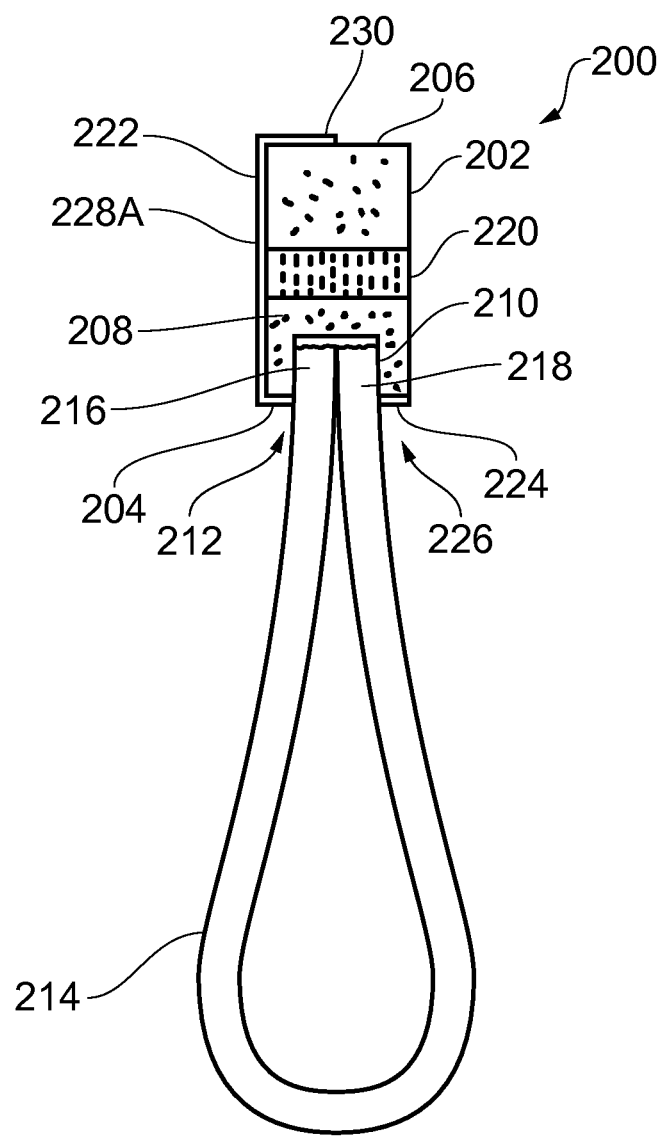
FIG. 3 shows a cross-section through the fragrance burner assembly shown in FIG. 2.

Some embodiments of the present invention will now be described with reference to FIGS. 2 and 3. FIGS. 2 and 3 shows a fragrance burner 200. The burner 200 includes a porous core of sintered metal 202. The porous metal core 202 is preferably made of sintered bronze. The porous metal core 202 is generally cylindrical in shape, and has a proximal end surface 204 and a distal end surface 206. A side surface 208 extends between the proximal end 204 and the distal end 206. The porous metal core 202 defines an interior volume, the major part of which is occupied by the porous metal. In addition, the porous metal core includes a void 210, arranged to provide an opening 212 in the proximal end surface 204 of the core 202.

The fragrance burner 200 also includes a wick 214. The wick 214 is preferably formed from a length of rope-like fabric. The wick 214 includes a first end 216 and a second end 218. The ends 216, 218 of the wick 214 are located in the void 210 of the porous metal core 202. The diameter of the wick 214 is such that both ends 216, 218 of the wick may be inserted in the void 210. The wick 214 therefore forms a loop, which, in use, hangs in a fuel mixture. The length of the wick 214 is chosen to suit the fragrance burner in question. However, a typical length is around 12 cm.

The fragrance burner 200 also includes a metal surround 220. The metal surround 220 forms a ring around the porous metal core 202. The metal surround 220 is positioned on or adjacent the side surface 208. The metal surround 220 has a width that is approximately equal to one third of the height of the porous metal core 202. The diameter measured between the inner surface of the metal surround is approximately the same as the diameter of the cylinder of the porous metal core 202. During the manufacturing process, the metal surround 220 is wrapped around the porous metal core 202, and held in place using pins (not shown).

The metal surround 220 is coated in a catalyst. The catalyst is preferably platinum, palladium, lanthanum or manganese oxide, or a mixture thereof. These materials have a relatively high thermal activity, meaning a smaller quantity of the catalyst can be used. As catalysts tend to be expensive metals, this will enable lower final product unit cost to be achieved.

The process of depositing the catalyst on the metal surround will be described in the following. The catalyst is coated on the metal surround 220 by electroplating, or to achieve a rougher surface (and thus greater surface area), wash coating can be used. Wash coating is generally used in car catalytic converters. The catalytic particles are suspended in a liquid which is then coated onto the metal substrate. The process of coating a catalyst is otherwise well known, and will not be described here in any further detail.

The fragrance burner 200 also includes a metal housing 222. The metal housing 222 is arranged to hold the various components of the fragrance burner 200 together. The metal housing 222 includes a proximal end plate 224. The proximal end plate 224 is a disc having an axial opening 226 that is slightly smaller in diameter than the void 210. This enables the proximal end plate to provide a gentle grip on the ends of the wick 214. The metal housing 222 also includes upwardly extending securing arms 228A, 228B, 228C. These arms are connected to an outer edge of the proximal end plate 224, and are positioned equidistant from each other. The length of the arms is the same as the height of the cylinder of the porous metal core 202 plus the radius of the porous metal core 202. The ends of the arms include pin-holes suitable for accepting an anchor pin 230. During the manufacture process, the arms 228A, 228B, 228C are bent upwards to form an angle of 90° to the plane of the proximal end plate 224. The arms 228A, 228B, 228C are accordingly positioned on the side surface 208 of the porous metal core 202. The arms 228A, 228B, 228C are bent again so that their ends are positioned against the distal end 206 of the core. The anchor pin 230 is then inserted through all of the pin-holes of the arms to anchor the metal housing 222 to the porous metal core 202. It will be appreciated that the metal housing 222 is just one way in which the burner 200 is held together. Other mechanisms may be used as appropriate.

In the above-described embodiment, the porous metal core 202 is a sintered metal. Preferably the metal is bronze. Other metals may be used, such as copper, stainless steel, nickel bronze or tin bronze. Additional plating such as nickel may be used to hinder corrosion and/or enhance the aesthetics of the material.

A sintered material is a monolithic material with a fused granular structure, resulting in a porosity defined by the particle size of the material grains used. Sintered materials may be characterised by their porosity. Typically sintered stainless steel would have a porosity of 35% and bronze would have a porosity of 50%. In some embodiments, the particle size must be adequate to create an open cell structure, through which gas or liquid may flow.

Sintered materials are formed from powder, granules or balls of a pre-selected size, which are partially fused together by bringing the material close to its melting point. When the material is close to its melting point, atoms in the material diffuse across the boundaries of the particles, which creates one solid object. The extent of this diffusion and densification determines the pore size of the resultant object. Pore sizes may range from 1 to 300 microns, with most sintered materials typically being within the range of 5 to 150 microns. An ideal size for the catalytic burner would be within the range of 15 to 150 microns, with an optimal size being in the range of 30 to 100 microns.

Through selection of appropriately sized granules and with accurate densification, the resultant pore size may be accurately controlled, which is not the case with production methods of other porous structures. This ability to accurately determine the pore size, coupled with the materials' innate resistance to heat, makes sintered materials an ideal choice for use in catalytic burner heads. Sintered materials are particularly suited for use with the aromatic, and sometimes viscous, oils used by catalytic burners. The operating temperature of a catalytic burner, in the range of 230 to 280° C., is far below the sintering point of the sintered materials.

In the embodiment shown in FIGS. 2 and 3, the catalyst is deposited on the metal surround 120. In an alternative embodiment, the fragrance burner does not include the metal surround 220, and the catalyst is deposited on the sintered metal itself. It is possible to apply a washcoat using the actual catalyst, such as Pt/Al2O3. Additionally, it is possible to contact the sintered material directly with a solution of a noble metal salt (such as Pt or Pd salt) for deposition of the respective catalyst.

Figure 4:
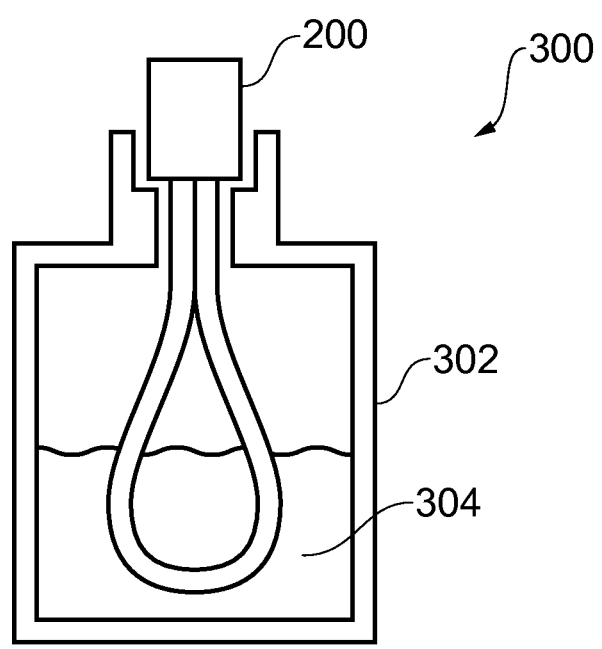
FIG. 4 shows a cross-section through a fragrance burner in accordance with a some embodiments described herein.

FIG. 4 shows a catalytic burner 300 in accordance with some embodiments of the present invention. The burner 300 includes the burner assembly 200, described above in connection with FIGS. 2 and 3. The burner assembly is positioned in the neck of a fuel reservoir 302. The fuel reservoir 302 includes fuel 304, into which the wick of the assembly 200 hangs during use.

Figure 5:
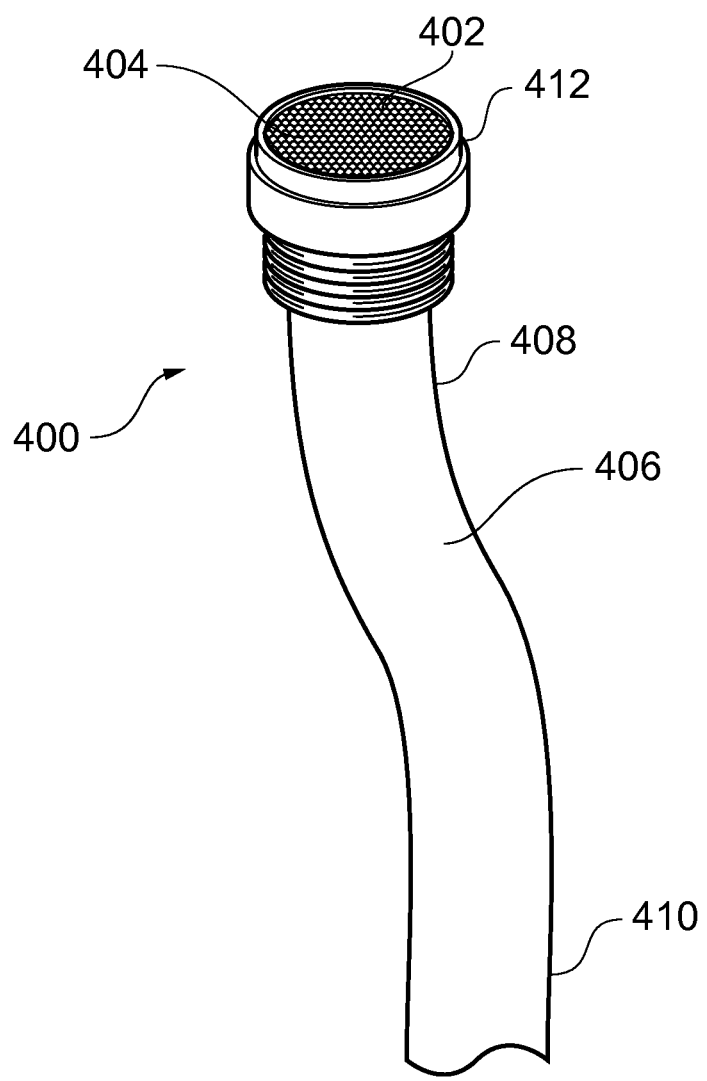
FIG. 5 shows a perspective view a fragrance burner assembly in accordance with a some embodiments described herein.

Some embodiments of the present invention will now be described with reference to FIG. 5. FIG. 5 shows a fragrance burner 400. The fragrance burner differs from that described in the first embodiment in that it does not include the metal surround 220, and the metal housing 222 takes a different form, as will be described below. The fragrance burner 400 is an example of a burner in which the catalyst is deposited on the core itself. The burner 400 includes a porous core of sintered metal 402. The porous metal core 402 is preferably made of sintered bronze. The porous metal core 402 is generally cylindrical in shape, and has a proximal end surface (not shown) and a distal end surface 404. A side surface (not shown) extends between the proximal end and the distal end 404. The porous metal core 402 defines an interior volume, the major part of which is occupied by the porous metal.

The fragrance burner 400 also includes a wick 406. The wick 406 is preferably formed from a length of rope-like fabric. The wick 406 includes a first end 408 and a second end 410. The first end 408 of the wick 406 is positioned in communication with the core 402, as will be described in more detail below. The second end 410 is arranged to hang in the fuel reservoir (not shown).

The fragrance burner 402 also includes a metal housing 412. The metal housing 412 is arranged to hold the various components of the fragrance burner 402 together. The metal housing 412 is a hollow bolt, into which the porous metal core 402 and the wick 406 are placed. The bolt 412 has proximal and distal axial openings. The proximal opening is slightly smaller in diameter than wick 406. This enables the proximal end to provide a gentle grip on the end 408 of the wick 406. The porous metal core 402 sits within the distal opening of the bolt 412. The diameter of the wick 406 is such that the first end 408 of the wick may be inserted in the hollow bolt 412. The length of the wick 406 is chosen to suit the fragrance burner in question. However, a typical length is around 6 cm.

The porous metal core 402 is coated in a catalyst. The catalyst is preferably platinum, palladium, lanthanum or manganese oxide, or a mixture thereof. These materials have a relatively high thermal activity, meaning a smaller quantity of the catalyst can be used. As catalysts tend to be expensive metals, this will enable lower final product unit cost to be achieved.

The process of depositing the catalyst on the porous metal core 402 will be described in the following. The catalyst is coated on the porous metal core 402 by electroplating, or to achieve a rougher surface (and thus greater surface area), wash coating can be used. Wash coating is generally used in car catalytic converters. The catalytic particles are suspended in a liquid which is then coated onto the metal substrate. The process of coating a catalyst is otherwise well known, and will not be described here in any further detail.

In the above-described embodiment, the porous metal core 202, 402 is a sintered metal. Preferably the metal is bronze. Other metals may be used, such as copper, stainless steel, nickel bronze or tin bronze. Additional plating such as nickel may be used to hinder corrosion and/or enhance the aesthetics of the material.

A sintered material is a monolithic material with a fused granular structure, resulting in a porosity defined by the particle size of the material grains used. Sintered materials may be characterised by their porosity. Typically sintered stainless steel would have a porosity of 35% and bronze would have a porosity of 50%. In some embodiments, the particle size must be adequate to create an open cell structure, through which gas or liquid may flow.

Sintered materials are formed from powder, granules or balls of a pre-selected size, which are partially fused together by bringing the material close to its melting point. When the material is close to its melting point, atoms in the material diffuse across the boundaries of the particles, which creates one solid object. The extent of this diffusion and densification determines the pore size of the resultant object. Pore sizes may range from 1 to 300 microns, with most sintered materials typically being within the range of 5 to 150 microns. An ideal size for the catalytic burner would be within the range of 15 to 150 microns, with an optimal size being in the range of 30 to 100 microns.

Through selection of appropriately sized granules and with accurate densification, the resultant pore size may be accurately controlled, which is not the case with production methods of other porous structures. This ability to accurately determine the pore size, coupled with the materials' innate resistance to heat, makes sintered materials an ideal choice for use in catalytic burner heads. Sintered materials are particularly suited for use with the aromatic, and sometimes viscous, oils used by catalytic burners. The operating temperature of a catalytic burner, in the range of 230 to 280° C., is far below the sintering point of the sintered materials.

In the embodiment shown in FIGS. 2 and 3, the catalyst is deposited on the metal surround 120. In an alternative embodiment, the fragrance burner does not include the metal surround 220, and the catalyst is deposited on the sintered metal itself. It is possible to apply a washcoat using the actual catalyst, such as Pt/Al2O3. Additionally, it is possible to contact the sintered material directly with a solution of a noble metal salt (such as Pt or Pd salt) for deposition of the respective catalyst.

One possible advantage of some embodiments may a burner that can be started within around twenty seconds using a match or cigarette lighter, or within around ten seconds using a jet-type cigarette lighter. This also avoids the presence of a four to six inch flame which is typically present with ceramic stone burners. Typical ceramic burners take upwards of three minutes to start. This is because the catalyst and the metal core reach a suitable operating temperature much more quickly than a ceramic stone.

One possible advantage of some embodiments may include that, because the metal burner conducts heat much more efficiently than ceramic, the burner 200 has a more stable temperature. This avoids the process of incomplete combustion which is found in ceramic burners, and hence charring is avoided. Furthermore, the greater pore size of the sintered metal means blocking is essentially impossible.

In some embodiments, the core is described as being generally cylindrical. In an alternative embodiment, the core may be a cuboid, or any other suitable shape.

It will be appreciated that the term "fragrance burner" may refer to the combination of the wick and the metal core alone. Alternatively, the term "fragrance burner" may refer to the combination of the wick, the metal core and the fuel reservoir.

In the above described embodiments, the burner includes a porous metal core. In a preferred embodiment, the porous metal core is made of a sintered metal, such as sintered bronze. Furthermore, the porous core may also be made of a non-metallic sintered material, such as a sintered ceramic. The advantages described above in connection with sintered metal, also exist for non-metallic sintered material. Whilst in the embodiment described above, it is preferred to have a porous metal core made of sintered material, in other embodiments, the porous metal core may not be sintered. For example, as an alternative to sintering, the porous metal core may be manufactured using electric pulse consolidation or other similar techniques.

Whilst the above embodiments are described with reference to fragrance burners, it will be appreciated that the present invention is not limited to burning hydrocarbons which contain fragrance. In alternative embodiments, the catalytic burner assemblies described herein may be used to burn non-fragrant (odourless) liquids, such as pure alcohol. A further benefit of the present invention is that the catalytic combustion of liquid (fragrant or odourless) acts to purify air in the vicinity of the burner. Accordingly, the catalytic burner assemblies described herein can be used simply as air purifiers alone by catalytically combusting odourless liquid fuel, or alternatively both to purify the air and provide fragrance thereto by catalytically combusting fragrant liquid fuel.

What is claimed is:

1. A catalytic burner assembly, comprising:
    a porous sintered metal core having a fused granular structure;
    a catalyst, deposited on or around the core; and
    a wick, in communication with the core, and arranged to draw fuel to the core.

2. The burner assembly according to claim 1, wherein the sintered metal is bronze.

3. The burner assembly according to claim 1, wherein the porous core has a porosity greater than 30%.

4. The burner assembly according to claim 1, wherein the porous core has pore sizes from 15 to 150 microns.

5. The burner assembly according to claim 1, wherein the catalyst is deposited on the porous sintered metal core.

6. The burner assembly according to claim 1, further comprising: a metal substrate, positioned on or adjacent the porous sintered metal core; wherein the catalyst is deposited on the metal substrate.

7. The burner assembly according to claim 1, wherein said porous sintered metal core is substantially cylindrical.

8. The burner assembly according to claim 7, wherein said porous sintered metal core comprises a void, located at an end of the core, at least a first end of the wick being positioned within said void.

9. The burner assembly according to claim 1, wherein said catalyst is platinum, palladium, lanthanum or a manganese oxide.

10. The burner assembly according to claim 1, further comprising: a housing, arranged to hold the porous sintered metal core and the wick together.

11. The burner assembly according to claim 1, wherein the burner assembly is a fragrance burner assembly.

12. The burner assembly according to claim 1, further comprising:
    a fuel reservoir, having an opening, wherein, in use, the burner assembly is positioned in the opening, and an end of the wick is positioned within the fuel reservoir.

13. A method of manufacturing a catalytic burner assembly, comprising:
    providing a porous sintered metal core having a fused granular structure;
    providing a catalyst on or around the core; and
    providing a wick in a communication with the core.

14. The method of manufacture according to claim 13, wherein said step of providing a catalyst on or around the porous sintered metal core includes a step of depositing a catalyst on the core.

15. The burner assembly according to claim 1, wherein the pores of the porous sintered metal core extend from a first end to an opposite second end.

16. The burner assembly according to claim 6, wherein the metal substrate is a band wrapped around the porous sintered metal core.

17. The burner assembly according to claim 1, wherein the porous metal sintered metal core is a solid body.

18. The burner assembly according to claim 1, wherein the catalyst is coated on the porous sintered metal core.

19. The burner assembly according to claim 1, wherein the porous sintered metal core includes pores having an open cell structure.

20. The burner assembly according to claim 1, wherein a majority of a body of the porous sintered metal core is porous.

* * * * *